US010751123B2

United States Patent
Leuthardt et al.

(10) Patent No.: US 10,751,123 B2
(45) Date of Patent: Aug. 25, 2020

(54) THERMOABLATION PROBE

(71) Applicants: WASHINGTON UNIVERSITY, St. Louis, MO (US); BOARD OF TRUSTEES OF SOUTHERN ILLINOIS UNIVERSITY, Edwardsville, IL (US)

(72) Inventors: Eric Leuthardt, St. Louis, MO (US); Jenna Gorlewicz, Edwardsville, IL (US); Mahmood Rezapour, Glen Carbon, IL (US)

(73) Assignees: Washington University, St. Louis, MO (US); Board of Trustees of Southern Illinois University, Edwardsville, IL (US)

( * ) Notice: Subject to any disclaimer, the term of this patent is extended or adjusted under 35 U.S.C. 154(b) by 67 days.

(21) Appl. No.: 15/336,887

(22) Filed: Oct. 28, 2016

(65) Prior Publication Data

US 2017/0119467 A1     May 4, 2017

Related U.S. Application Data

(60) Provisional application No. 62/248,917, filed on Oct. 30, 2015.

(51) Int. Cl.
| | | |
|---|---|---|
| *A61B 18/22* | (2006.01) | |
| *A61B 18/00* | (2006.01) | |
| *A61B 18/20* | (2006.01) | |
| *A61B 90/00* | (2016.01) | |

(52) U.S. Cl.
CPC .... *A61B 18/22* (2013.01); *A61B 2018/00023* (2013.01); *A61B 2018/00446* (2013.01); *A61B 2018/00577* (2013.01); *A61B 2018/00714* (2013.01); *A61B 2018/00821* (2013.01); *A61B 2018/2005* (2013.01); *A61B 2018/2238* (2013.01); *A61B 2018/2288* (2013.01); *A61B 2090/3762* (2016.02)

(58) Field of Classification Search
None
See application file for complete search history.

(56) References Cited

U.S. PATENT DOCUMENTS

| | | | |
|---|---|---|---|
| 6,572,608 B1 * | 6/2003 | Lee | A61F 9/008 606/13 |
| 6,770,070 B1 * | 8/2004 | Balbierz | A61B 10/04 600/566 |
| 7,371,210 B2 | 5/2008 | Brock et al. | |
| 7,922,645 B2 * | 4/2011 | Kaplan | A61B 17/3468 600/3 |
| 8,152,756 B2 * | 4/2012 | Webster | A61B 17/3417 604/95.01 |
| 8,308,722 B2 | 11/2012 | Ormsby et al. | |

(Continued)

FOREIGN PATENT DOCUMENTS

WO     WO 2015073943 A1 *   5/2015   ......... A61N 1/36017

*Primary Examiner* — Carl H Layno
*Assistant Examiner* — Manolis Pahakis
(74) *Attorney, Agent, or Firm* — Armstrong Teasdale LLP

(57) ABSTRACT

A thermoablation probe for performing an interstitial thermal therapy (ITT) procedure on a brain lesion generally includes a rigid sheath and a flexible treatment device telescopically slidable within the sheath. The treatment device has a substantially continuous covering and a shape-memory wire enveloped by the covering.

7 Claims, 4 Drawing Sheets

(56) References Cited

U.S. PATENT DOCUMENTS

| | | | |
|---|---|---|---|
| 8,728,092 B2 | 5/2014 | Qureshi et al. | |
| 8,747,418 B2 | 6/2014 | Qureshi et al. | |
| 8,968,287 B2 | 3/2015 | Shroff et al. | |
| 8,979,871 B2 | 3/2015 | Tyc et al. | |
| 8,992,523 B2 | 3/2015 | Pellegrino et al. | |
| 9,023,020 B2 | 5/2015 | Scheller et al. | |
| 9,023,026 B2 | 5/2015 | Prakash | |
| 9,078,666 B2 | 7/2015 | Okada | |
| 2002/0077627 A1* | 6/2002 | Johnson | A61B 18/1477 606/41 |
| 2002/0111618 A1* | 8/2002 | Stewart | A61B 18/1492 606/41 |
| 2003/0028114 A1* | 2/2003 | Casscells, III | A61B 5/0077 600/474 |
| 2003/0130711 A1* | 7/2003 | Pearson | A61B 18/1477 607/101 |
| 2004/0210289 A1* | 10/2004 | Wang | A61K 9/5094 607/116 |
| 2006/0004348 A1* | 1/2006 | Scheller | A61B 18/22 606/4 |
| 2006/0178666 A1* | 8/2006 | Cosman | A61B 18/148 606/41 |
| 2008/0009747 A1* | 1/2008 | Saadat | A61B 1/04 600/471 |
| 2008/0097193 A1* | 4/2008 | Karmarkar | A61B 5/055 600/423 |
| 2009/0036823 A1* | 2/2009 | LePivert | A61B 18/02 604/21 |
| 2009/0118610 A1* | 5/2009 | Karmarkar | A61B 5/0476 600/420 |
| 2009/0137952 A1* | 5/2009 | Ramamurthy | G01L 1/242 604/95.01 |
| 2009/0240242 A1 | 9/2009 | Neuberger | |
| 2010/0125269 A1* | 5/2010 | Emmons | A61B 18/18 606/33 |
| 2010/0274178 A1* | 10/2010 | LePivert | A61M 25/0045 604/21 |
| 2011/0319910 A1 | 12/2011 | Roelle et al. | |
| 2012/0010490 A1* | 1/2012 | Kauphusman | A61N 1/056 600/373 |
| 2012/0089047 A1* | 4/2012 | Ryba | A61B 18/02 600/554 |
| 2012/0330180 A1* | 12/2012 | Pellegrino | A61B 17/3472 600/547 |
| 2013/0030408 A1 | 1/2013 | Piferi et al. | |
| 2013/0035537 A1* | 2/2013 | Wallace | A61B 34/30 600/8 |
| 2013/0116683 A1* | 5/2013 | Shadduck | A61B 17/32037 606/41 |
| 2013/0303876 A1* | 11/2013 | Gelfand | A61N 1/36057 600/407 |
| 2013/0310823 A1* | 11/2013 | Gelfand | A61B 18/18 606/33 |
| 2014/0012155 A1* | 1/2014 | Flaherty | A61B 5/015 600/549 |
| 2014/0018788 A1* | 1/2014 | Engelman | A61B 18/18 606/33 |
| 2014/0228831 A1* | 8/2014 | Fischer | A61B 18/02 606/21 |
| 2014/0276703 A1* | 9/2014 | McKay | A61B 18/02 606/21 |
| 2014/0276713 A1* | 9/2014 | Hoey | A61B 18/04 606/27 |
| 2015/0087961 A1 | 3/2015 | Tyc et al. | |
| 2015/0087962 A1 | 3/2015 | Tyc et al. | |
| 2015/0087963 A1 | 3/2015 | Tyc et al. | |
| 2015/0088108 A1 | 3/2015 | Tyc et al. | |
| 2015/0099936 A1* | 4/2015 | Burdulis | A61M 25/0194 600/204 |
| 2015/0100052 A1* | 4/2015 | Wang | A61B 18/1482 606/34 |
| 2015/0157401 A1* | 6/2015 | Falwell | A61B 18/1492 606/41 |
| 2015/0157405 A1 | 6/2015 | Beeckler | |
| 2015/0202008 A1 | 7/2015 | Grant et al. | |
| 2015/0216599 A1 | 8/2015 | Tyc et al. | |
| 2015/0265216 A1* | 9/2015 | Andrews | A61B 6/0421 128/845 |
| 2016/0287308 A1* | 10/2016 | Grant | A61B 18/02 |
| 2016/0287334 A1* | 10/2016 | Grant | A61B 18/02 |
| 2016/0296267 A1* | 10/2016 | Neimat | A61N 1/36017 |
| 2016/0331446 A1* | 11/2016 | Martin | A61B 18/1492 |
| 2017/0056616 A1* | 3/2017 | Leeflang | A61M 25/0012 |

\* cited by examiner

THERMOABLATION PROBE

CROSS REFERENCE TO RELATED APPLICATION

This application claims the benefit of U.S. Provisional Patent Application Ser. No. 62/248,917 entitled THERMOABLATION PROBE filed on Oct. 30, 2015, the entirety of which is hereby incorporated by reference.

BACKGROUND

The present disclosure relates generally to thermoablation probes and, more particularly, to thermoablation probes for treating brain lesions.

At least some known thermoablation procedures for brain lesions are considered interstitial thermal therapy (ITT) procedures by which brain lesions are heated from within. However, conventional thermoablation probes for performing an ITT procedure on a brain lesion are rigid, shaft-like structures deployable within the lesion only along a straight-line path. While these straight-line probes can be effective at radiating the regions of the lesion that are immediately adjacent the linear path of deployment, these probes are relatively ineffective at treating peripheral regions of the lesion that are offset from the linear path of deployment beyond the range of the probe's radiant energy.

It would be useful, therefore, to provide a more versatile thermoablation probe for effectively treating brain lesions of various shapes and sizes.

SUMMARY

In one aspect, a thermoablation probe for performing an interstitial thermal therapy (ITT) procedure on a brain lesion generally comprises a rigid sheath and a flexible treatment device telescopically slidable within the sheath. The treatment device has a substantially continuous covering and a shape-memory wire enveloped by the covering.

In another aspect, a thermoablation probe for performing an interstitial thermal therapy (ITT) procedure on a brain lesion generally comprises a rigid sheath and a flexible treatment device telescopically slidable within the sheath. The treatment device is deployable from the sheath along a curvature axis having a plurality of predefined target points.

In yet another aspect, a thermoablation probe for performing an interstitial thermal therapy (ITT) procedure on a brain lesion generally comprises a rigid sheath and a flexible treatment device telescopically slidable within the sheath. The treatment device is pre-curved such that, when the treatment device is deployed from the sheath, the treatment device automatically follows a predefined curvature axis.

BRIEF DESCRIPTION OF THE DRAWINGS

Corresponding reference characters indicate corresponding parts throughout the several views of the drawings.

DETAILED DESCRIPTION OF THE DRAWINGS

Intracranial lesions such as brain tumors and epileptic foci are often targets for medical therapy, surgical resection, and radiotherapy. However, many therapeutic targets are not surgically accessible via traditional procedures due to the morbidity and/or mortality associated with surgical excision. Treatment options for patients with surgically inaccessible lesions have generally been limited to medical therapy and radiotherapy.

A minimally-invasive surgical treatment for deep brain lesions that facilitates avoiding the morbidities associated with surgical resection is highly desirable. The embodiments set forth herein facilitate minimally-invasive thermoablation procedures to treat lesions in a variety of organ systems, including tumors of the brain. For example, the embodiments set forth herein facilitate performing a laser interstitial thermal therapy (LITT) procedure in a manner that yields a more precise and minimally-invasive heat injury to target tissue. In that regard, the embodiments set forth herein provide improvements over straight-line laser probes for LITT procedures. While preoperative planning can enable surgeons to choose the most optimal path for placement of a straight-line laser probe, straight-line laser probes tend to limit the treatment profile that is able to be achieved. Because brain tumors, for example, are often quite large and have complex geometries, or may occur in multiple locations, the inability to ablate an entire brain tumor is commonplace with straight-line laser probes.

Figure 1:
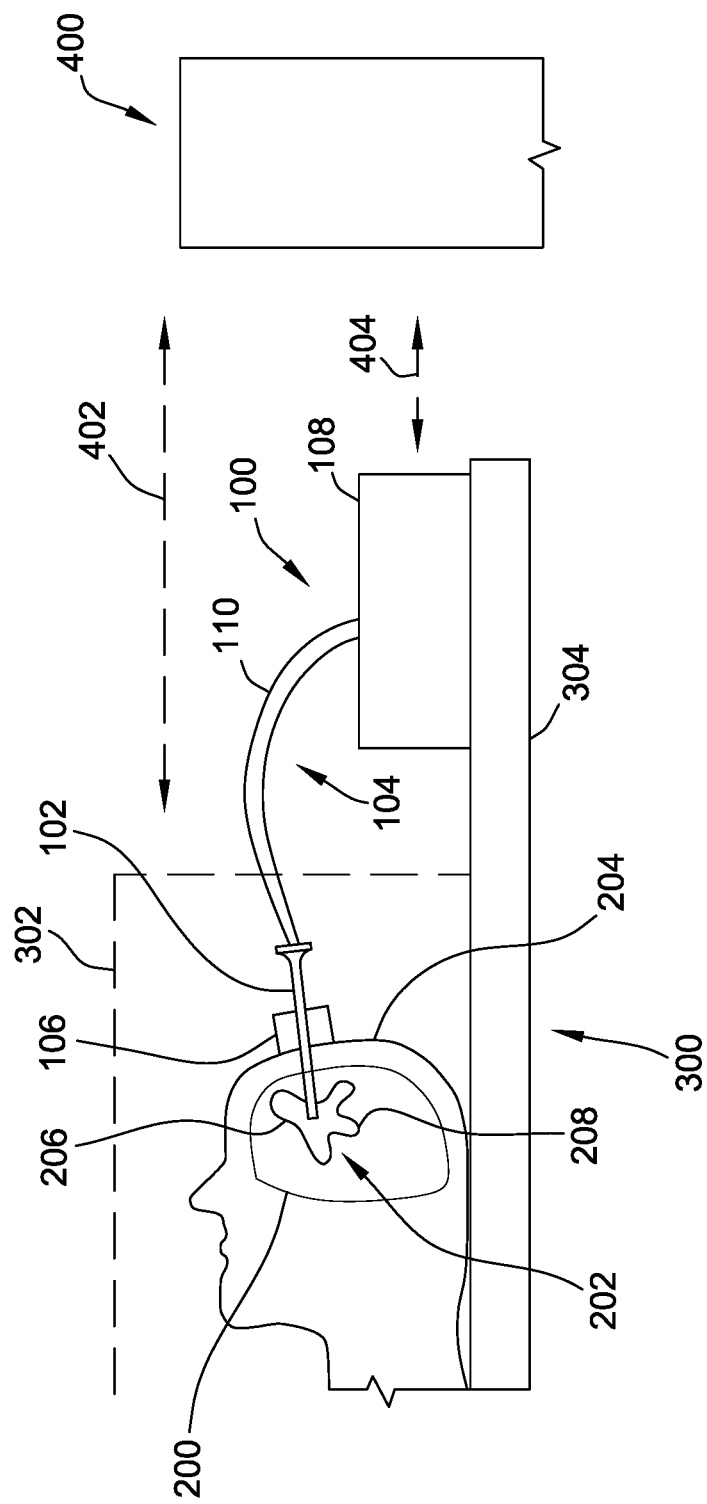
FIG. 1 is a schematic illustration of a system for performing a thermoablation procedure on a lesion in the brain of a patient.

FIG. 1 illustrates one suitable embodiment of a probe system (indicated generally at 100) for performing a thermoablation procedure on the brain 200 of a patient (e.g., an ITT procedure to ablate a brain lesion such as, for example, a brain tumor indicated generally at 202). In other embodiments, the probe system 100 may be useful to perform any suitable thermoablation procedures or other types of procedures (e.g., exploratory procedures) on any suitable organs of the patient's body.

The illustrated probe system 100 has a probe 102 and a probe handling device (indicated generally at 104) to facilitate operating the probe 102 during the ITT procedure. The probe handling device 104 includes a probe mount 106, a probe control unit 108, and at least one conduit 110 (e.g., electrical wire(s), fluid tube(s), etc.) operatively connecting the probe control unit 108 to the probe 102 and the probe mount 106. The probe mount 106 is a mechanism which is operable (e.g., remotely controllable) to manipulate the position of the probe 102 relative to the skull 204 of the patient. More specifically, as set forth in more detail below, when the probe 102 is attached to the probe mount 106, and the probe mount 106 is attached to the skull 204, the probe mount 106 is operable to maneuver the probe 102 relative to the skull 204 using automatic and/or manual controls (e.g., dials) on the probe control unit 108. In other embodiments, the probe handling device 104 may be configured in any suitable manner that facilitates enabling the probe 102 to function as described herein.

In the illustrated embodiment, the ITT procedure is guided by a magnetic resonance imaging (MRI) system (indicated generally at 300). The illustrated MRI system 300 includes a scanner 302 and a patient table 304 on which the probe control unit 108 is mounted such that the surgeon can stand beside the patient when manually positioning the probe 102 in relation to the skull 204 using the probe control unit 108. The scanner 302 provides the surgeon with real-time images of the brain 200 during the ITT procedure to facilitate proper positioning of the probe 102 in the tumor 202 using the probe mount 106 and the probe control unit 108. In other embodiments, the ITT procedure may be guided using any suitable imaging system (e.g., a computed tomography (CT) system). In other suitable embodiments, the ITT procedure may not be guided by an imaging system.

In the illustrated embodiment, a workstation (indicated generally at 400) serves as an interface between the MRI system 300 and the probe system 100 (i.e., the workstation 400 communicates 402 with the MRI system 300 in real-time, and the workstation 400 communicates 404 with the probe control unit 108 in real-time to provide the surgeon with aggregated data in furtherance of the ITT procedure). Notably, the workstation 400 and the probe control unit 108 each includes at least one computing device having a controller or processing device such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processing device capable of executing the functions described herein. Furthermore, the methods described herein may be encoded as executable instructions embodied in a computer readable medium, including, without limitation, a storage device and/or a memory device. Such instructions, when executed by the controller or processing device, cause the controller or processing device to perform at least a step of the methods described herein. The above examples are exemplary only, and thus are not intended to limit in any way the definition and/or meaning of the terms controller and processing device.

Figure 2:
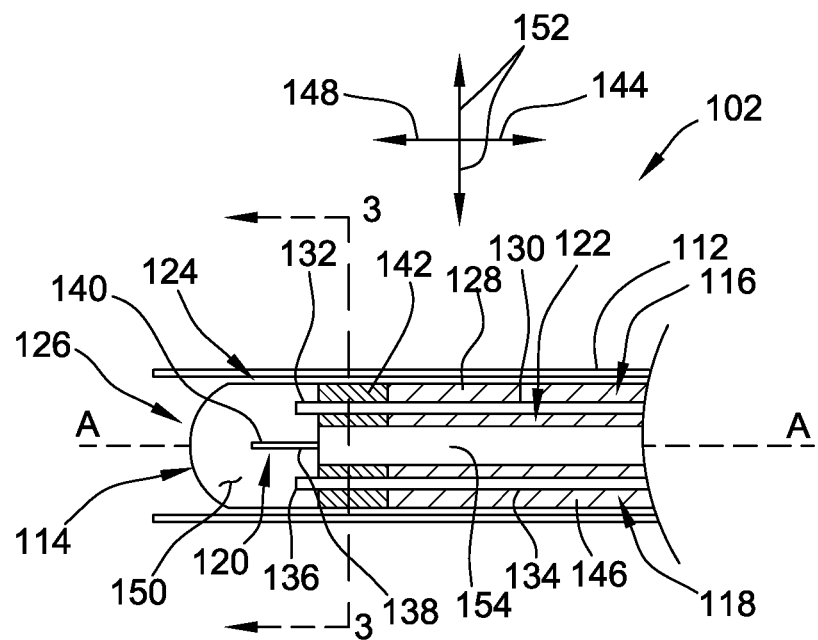
FIG. 2 is a schematic cross-sectional illustration of a probe in the system shown in FIG. 1.
Figure 3:
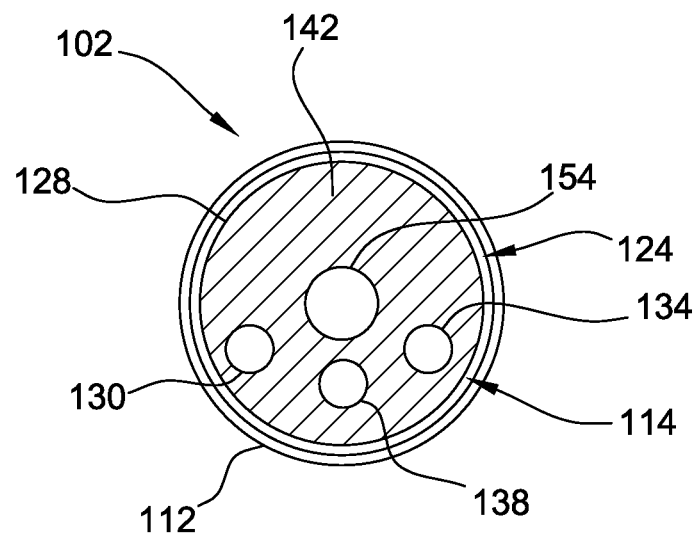
FIG. 3 is another schematic cross-sectional illustration of the probe shown in FIG. 2 and taken along plane 3-3 of FIG. 2.

With reference now to FIGS. 2 and 3, the probe 102 includes a tubular sheath 112 and an elongate treatment device (indicated generally at 114) telescopically slidable along the sheath 112. The sheath 112 is made of a rigid material (e.g., titanium), and the treatment device 114 is made of flexible materials, as set forth in more detail below. The illustrated treatment device 114 is a laser-type ablation device having a cooling structure (indicated generally at 116), a temperature sensing structure (indicated generally at 118), a radiating structure (indicated generally at 120), and a shaping structure (indicated generally at 122) that are collectively enveloped by a covering (indicated generally at 124). The covering 124 is made of a flexible material (e.g., a flexible plastic material) and has a tubular shape with an enclosed tip (indicated generally at 126).

The illustrated covering 124 has a substantially continuous outer surface 128 (e.g., the outer surface 128 is substantially smooth, and/or entirely free of edges or other discontinuities that could lacerate (or otherwise damage) brain tissue and/or disrupt the sliding motion of the treatment device 114 through the sheath 112). Optionally, the sheath 112 and the treatment device 114 may have any suitable sizes that facilitate their clinical application(s). For example, in the illustrated embodiment, the covering 124 has an outer diameter of about 2.8 millimeters and a thickness of about 0.1 millimeter, while the sheath 112 has an inner diameter of about 3.3 millimeters and a thickness of about 0.15 millimeters. Other sizes are also contemplated (e.g., the sheath 112 may have an outer diameter of about 2.2 millimeters in some embodiments).

The illustrated cooling structure 116 includes a flexible cooling fluid tube 130 (e.g., a heat pipe) which extends along the length of the covering 124 and has a distal end 132. The illustrated temperature sensing structure 118 includes a flexible thermocouple 134 which extends along the length of the covering 124 and has a distal end 136. The illustrated radiating structure 120 includes a laser fiber 138 (or other suitable optical fiber) which extends along the length of the covering 124 and has a distal end 140. Suitably, the cooling structure 130, the temperature sensing structure 118, and the radiating structure 120 are operatively connected to the probe control unit 108. For example, the cooling tube 130 may be connected in flow communication with a cooling fluid reservoir and a pump of the cooling structure 130 such that the pump is actuatable via the probe control unit 108 for selectively channeling cooling fluid to and from the distal tip 132 of the cooling tube 130. As another example, the laser fiber 138 may be connected to a laser light source of the radiating structure 120 such that the laser light source is actuatable via the probe control unit 108 for selectively transmitting associated electromagnetic energy to and from the distal tip 140 of the laser fiber 138. In other embodiments, the cooling structure 116, the temperature sensing structure 118, and the radiating structure 120 have any suitable component(s) configured in any suitable manner that facilitates enabling the probe 102 to function as described herein.

In the illustrated embodiment, the cooling tube 130, the thermocouple 134, and the laser fiber 138 are supported in spaced relation to one another inside the covering 124 by a spacer disc 142 located near the tip 126. In the proximal direction 144 from the spacer disc 142, the covering 124 is at least partially filled with an insulating material 146 that facilitates thermally isolating the cooling tube 130, the thermocouple 134, and the laser fiber 138 from one another. In the distal direction 148 from the spacer disc 142, the covering 124 defines a gas-filled chamber 150 in which the distal end 132 of the cooling tube 130, the distal end 136 of the thermocouple 134, and the distal end 140 of the laser fiber 138 are disposed. Notably, the distal end 140 of the laser fiber 138 extends beyond the distal end 132 of the cooling tube 130 and the distal end 136 of the thermocouple 134 within the chamber 150. The distal end 140 of the laser fiber 138 is thereby positioned to emit radiant energy (e.g., a laser beam) outward through the covering 124 in at least one radial direction 152 substantially without interference from the distal end 132 of the cooling tube 130 or the distal end 136 of the thermocouple 134, while the distal end 132 of the cooling tube 130 facilitates cooling the tip 126 and the distal end 136 of the thermocouple 134 facilitates gauging the temperature of the tip 126. In other embodiments, the cooling tube 130, the thermocouple 134, and the laser fiber 138 may be positioned relative to one another in any suitable manner that facilitates enabling the probe 102 to function as described herein.

In the illustrated embodiment, the shaping structure 122 of the treatment device 114 is a wire 154 made of a shape-memory material such as nickel-titanium (or "Nitinol"). The wire 154 is pre-curved in the sense that the wire 154 has been trained to remember a predefined curved shape (e.g., a generally parabolic, hyperbolic, or other arcuate shape). As set forth in more detail below, the wire 154 assumes its curved shape whenever the wire 154 is not otherwise under the influence of (or biased out of) its predefined curved shape by an overriding external force.

In the illustrated embodiment, the wire 154 extends along the covering 124 such that the wire 154 is surrounded by the insulating material 146 and is connected to the spacer disc 142. The cooling tube 130, the thermocouple 134, and the laser fiber 138 are thereby flexible in unison within the covering 124 in response to either the shape-memory tendency of the wire 154 or an external force applied to the treatment device 114 to override the shape-memory tendency of the wire 154 (e.g., the external force applied by the sheath 112 to override the shape-memory tendency of the wire 154 and cause the treatment device 114 to straighten when retracted into the sheath 112). Moreover, in the illustrated embodiment, the wire 154, the cooling tube 130, the thermocouple 134, and the laser fiber 138 are sealed (e.g., hermetically sealed) within the covering 124. Suitably, the wire 154 may have any size to facilitate its application (e.g., the wire 154 has a diameter of about 0.8 millimeters in the illustrated embodiment).

Figure 4:
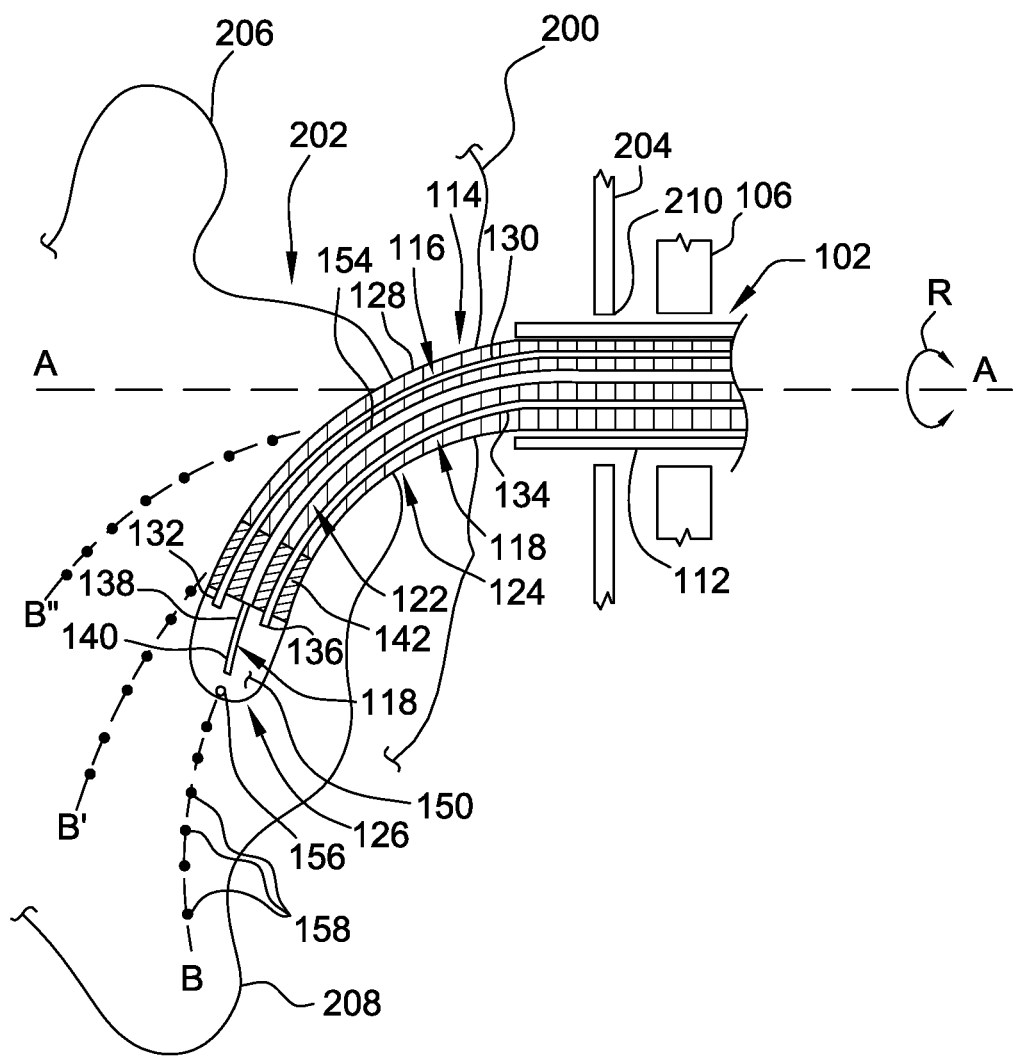
FIG. 4 is another schematic cross-sectional illustration of the probe shown in FIG. 2 when a treatment device of the probe is deployed.
Figure 5:
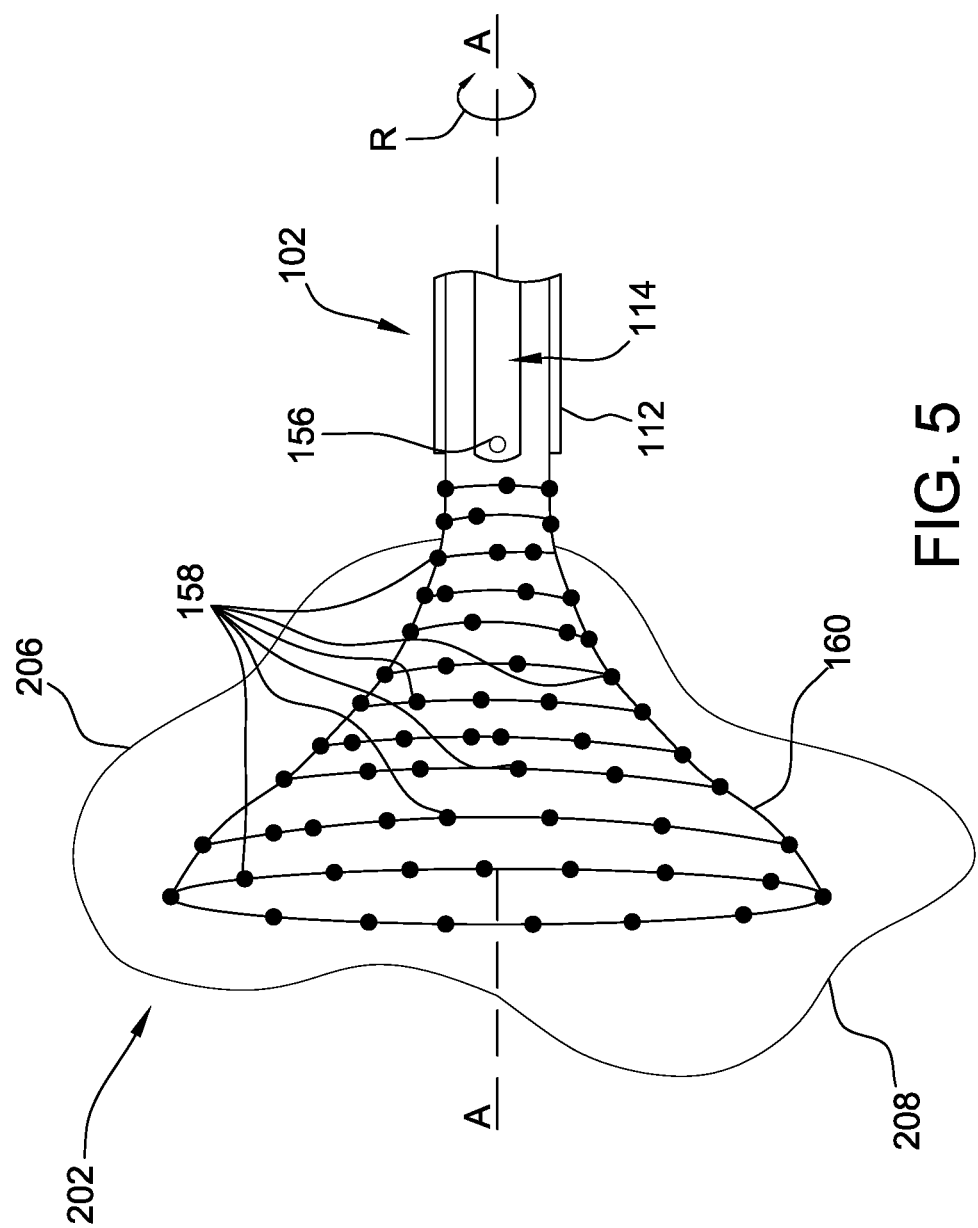
FIG. 5 is a schematic illustration of a treatment profile of the probe shown in FIG. 2 using the treatment device deployed as shown in FIG. 4.

Referring now to FIGS. 4 and 5, in order to perform the ITT procedure on the tumor 202 using the probe system 100, the probe mount 106 is fixed to the patient's skull 204 over a pre-drilled aperture 210 in the skull 204, and the probe 102 is inserted through the probe mount 106 and through the aperture 210 along an insertion axis A while the treatment device 114 is in its stowed state (which is shown in FIG. 2). Notably, the treatment device 114 is said to be in its stowed state when the tip 126 is retracted into the sheath 112 such that the tip 126 is protected from damage during insertion. By virtue of the sheath 112 being rigid, the sheath 112 overrides the pre-curved nature of the wire 154 such that the treatment device 114 is held in a linear orientation within the sheath 112 when the treatment device 114 is in its stowed state.

After the sheath 112 of the probe 102 has been inserted into the skull 204 to a desired depth (e.g., to a depth at which the sheath 112 is not inserted into the brain 200), the probe mount 106 is then locked in order to fix the sheath 112 in position such that the sheath 112 can no longer be moved along the insertion axis A without unlocking the probe mount 106. Once the sheath 112 is fixed in position along the insertion axis A, the tip 126 of the treatment device 114 is manually pushed out of the sheath 112 using the probe control unit 108 to convert the treatment device 114 from its stowed state (FIG. 2) to its deployed state (FIG. 4).

Because the wire 154 is pre-curved as set forth above, the treatment device 114 automatically deploys in a snake-like (or follow-the-leader) manner along a predefined curvature axis B having a generally arcuate (e.g., generally hyperbolic) shape. More specifically, if deployed at a controlled rate, a reference point 156 of the tip 126 automatically moves along a chain of predefined target points 158 of the curvature axis B. In this manner, the treatment device 114 is said to have a non-sweeping trajectory when deployed (and when retracted) such that the treatment device 114 provides for an automatic, more predictable, and more repeatable trajectory from one deployment to the next, and from one ITT procedure to the next (e.g., the curved trajectory and the end point are predictable with less than 0.5 millimeters of accuracy in the illustrated embodiment).

In the illustrated embodiment, the probe mount 106 and the probe control unit 108 are configured for reuse, while the probe 102 is not configured for reuse (i.e., the probe 102 is configured for one-time use and is made disposable). The probe 102 is, therefore, detachable from the probe mount 106 during the ITT procedure and/or after the completion of the ITT procedure. It is contemplated that the surgeon may be provided with a kit of different probes each for selective use in a different ITT procedure and/or during a different step in a single ITT procedure (e.g., some of the probes in the kit may have different sizes, and/or some of the probes in the kit may carry different instruments). For example, the kit may have a plurality of probes (each with a different curvature axis B, B', or B") for use in treating different lobes of a single tumor.

As shown in FIG. 5, the treatment device 114 is also rotatable about the insertion axis A (as indicated by rotational directions R) such that the curvature axis B likewise rotates about the insertion axis A, thereby defining a three-dimensional curved surface 160 of predefined target points 158. For example, as illustrated, if the curvature axis B has predefined target points 158 arranged in a generally hyperbolic shape (as shown in FIG. 4), then the surface 160 has target points 158 arranged in a generally half-hyperboloid shape (as shown in FIG. 5).

While the sheath 112 is illustrated in a fixed position relative to the probe mount 106 and the skull 204 along the insertion axis A, it should be noted that the interface between the sheath 112 and the probe mount 106 can be adjusted to selectively reposition and fix the sheath 112 in place along the insertion axis A as desired. In other words, the depth at which the sheath 112 is inserted into the patient's skull 204 is selectable by virtue of the sheath 112 being adjustably fixed to the probe mount 106. As such, the treatment device 114 has a different surface 160 of predefined target points 158 associated with each position of the sheath 112 along the insertion axis A, wherein the various surfaces 160 have the same shape but are axially offset from one another along the insertion axis A.

In this manner, the probe 102 is better able to treat the tumor 202, including the first lobe 206 and the second lobe 208 which are offset a distance from the insertion axis A. More specifically, because the tip 126 of the treatment device 114 can be deployed along a predefined curvature axis B in relation to the insertion axis A, the probe 102 enables the tip 126 to better treat (e.g., to more effectively radiate) peripheral regions of the tumor 202 that would otherwise be difficult to treat using conventional straight-line probes, such as first lobe 206 and second lobe 208.

When a brain lesion (e.g., a tumor), or a treatable mass generally, has an irregular shape, it can be difficult to ablate the peripheral regions of the lesion using an ITT probe that extends only linearly into the lesion. As illustrated in FIGS. 4 and 5, the above-described embodiments of a steerable ITT probe facilitate ablating regions of a tumor, for example, that are adjacent the insertion axis of the probe, as well as peripheral regions of the tumor that are spaced apart from the insertion axis of the probe beyond the range of the radiant energy emitted from the probe. Hence, the above-described embodiments facilitate improvements in probes for thermally treating lesions (or masses generally) in a variety of bodily systems.

Moreover, the above-described embodiments of an MRI-compatible, biocompatible, disposable probe serve as useful touch-up tools for LITT procedures. The illustrated probe includes a treatment device having a Nitinol wire backbone that is pre-curved for deploying along a follow-the-leader type of curved trajectory. This behavior is desirable, as it enables the treatment device to not sweep (or cut) healthy brain tissue in transit to compromised brain tissue that is the target of treatment.

The above-described embodiments further provide a probe that can be deployed, retracted, rotated, and then redeployed multiple times in a single surgical procedure. Suitably, the probe does not interfere with the thermometry readings taken during LITT procedures and otherwise causes minimal disruption to surgical workflow. Additionally, the probe embodiments facilitate procedures that are MRI-guided in real-time to treat a variety of conditions, including brain tumors, radiation necrosis, and epileptic foci. In this manner, a neurosurgeon is better able to precisely direct an MRI compatible, gas cooled, laser probe to a desired target. Once at the target, the neurosurgeon can administer LITT and monitor the thermal dose using real-time MRI thermometry data.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A thermoablation probe system for performing an interstitial thermal therapy (ITT) procedure on a brain lesion, said system comprising:
    a laser light source for generating and selectively transmitting ablative electromagnetic energy;
    a probe mount configured for attaching to a skull;
    an MRI compatible thermoablation probe configured for insertion through the probe mount and into the skull, the thermoablation probe comprising:
        a rigid sheath; and
        a flexible laser ablation device telescopically slidable within the sheath, wherein the flexible laser ablation device is coupled to the laser light source, wherein the laser ablation device is pre-curved to follow a predefined curvature trajectory upon deployment from the sheath, wherein the laser ablation device is configured for emitting the ablative electromagnetic energy along the predefined curvature trajectory upon the deployment, wherein the laser ablation device has a covering with an outer surface that is entirely free of edges and a shape-memory wire, a laser fiber, a thermocouple, a cooling tube and a distalmost gas-filled chamber, each hermetically sealed within the covering, and
    a control unit operatively coupled to the thermoablation probe and the probe mount; and
    wherein the probe mount is operable remotely by the control unit to maneuver the thermoablation probe relative to the skull.

2. The thermoablation probe system set forth in claim 1 wherein the laser ablation device is rotatable within the sheath to follow a predefined three-dimensional curved surface, along which the predefined curvature trajectory extends, upon deployment from the sheath.

3. The thermoablation probe system set forth in claim 1 wherein the shape-memory wire is made of nickel-titanium.

4. The thermoablation probe system set forth in claim 1 wherein the laser ablation device has insulating material that surrounds the wire within the covering.

5. The thermoablation probe system set forth in claim 1 wherein the laser ablation device is deployable from the sheath along a three-dimensional curved surface comprising the plurality of predefined target points.

6. The thermoablation probe system set forth in claim 1, wherein the covering is tubular.

7. The thermoablation probe system set forth in claim 1 wherein the shape-memory wire is made of a shape-memory alloy.

* * * * *